(12) United States Patent
Kawata et al.

(10) Patent No.: US 8,722,404 B2
(45) Date of Patent: May 13, 2014

(54) SHEET FOR GUIDING REGENERATION OF MESENCHYMAL TISSUE AND PRODUCTION METHOD THEREOF

(75) Inventors: Toshitsugu Kawata, Aki-gun (JP); Kaoru Tenjo, Hiroshima (JP); Koichiro Tsuji, Hiroshima (JP); Katsuyuki Yamanaka, Hasunuma-cho (JP)

(73) Assignees: GC Corporation, Tokyo (JP); Two Cells Co. Ltd., Hiroshima (JP)

( * ) Notice: Subject to any disclaimer, the term of this patent is extended or adjusted under 35 U.S.C. 154(b) by 1068 days.

(21) Appl. No.: 12/709,748

(22) Filed: Feb. 22, 2010

(65) Prior Publication Data

US 2010/0158982 A1   Jun. 24, 2010

Related U.S. Application Data

(62) Division of application No. 11/256,107, filed on Oct. 24, 2005, now abandoned.

(30) Foreign Application Priority Data

Oct. 25, 2004   (JP) ................................ 2004-309878

(51) Int. Cl.
| | |
|---|---|
| *C12N 5/077* | (2010.01) |
| *C12N 5/0789* | (2010.01) |
| *C12N 5/0797* | (2010.01) |
| *C12N 5/02* | (2006.01) |
| *A61F 2/00* | (2006.01) |
| *A61F 2/02* | (2006.01) |

(52) U.S. Cl.
USPC .......................................... 435/395; 424/426

(58) Field of Classification Search
USPC .......................................... 435/395; 424/426
See application file for complete search history.

(56) References Cited

U.S. PATENT DOCUMENTS

| | | |
|---|---|---|
| 2003/0138950 A1 | 7/2003 | McAllister et al. |
| 2006/0088569 A1 | 4/2006 | Kawata et al. |
| 2007/0248998 A1 | 10/2007 | Zhang |
| 2008/0220521 A1 | 9/2008 | Kawata et al. |

OTHER PUBLICATIONS

Rodriguez et al. 2000. Mesenchymal stem cells from osteoporotic patients produce a type I collagen-deficient extracellular matrix favoring adipogenic differentiation. Journal of Cell Biochemistry vol. 79, No. 4, pp. 557-565.*

Carnes et al. 1997. Cells with osteoblastic phenotypes can be explanted from human gingiva and periodontal ligament. Journal of Periodontology, vol. 68, No. 7, pp. 701-707.*

* cited by examiner

*Primary Examiner* — Jon P Weber
*Assistant Examiner* — Kailash C Srivastava
(74) *Attorney, Agent, or Firm* — Oblon, Spivak, McClelland, Maier & Neustadt, L.L.P.

(57) ABSTRACT

Method for regeneration of mesenchymal tissue from mesenchymal cells on a porous sheet composed of bioabsorbable polymer material.

7 Claims, No Drawings

SHEET FOR GUIDING REGENERATION OF MESENCHYMAL TISSUE AND PRODUCTION METHOD THEREOF

This application is a divisional of U.S. Ser. No. 11/256,107 filed Oct. 24, 2005, abandoned and claims the benefit of JP 2004-309878 filed Oct. 25, 2004.

BACKGROUND OF THE INVENTION

1. Field of the Invention

The present invention relates to a sheet for guiding regeneration of mesenchymal tissue, which is used when treating a deficit part of the mesenchymal tissue such as a bone, a cartilage, a muscle, fat or the like by a regeneration guide method, and a production method thereof.

2. Description of the Conventional Art

Realizing a medical treatment for regenerating biotissue and an organ in which there is a functional disorder or tissue/organ failure, is required. The regenerative medical treatment is a new medical treatment technique for reproducing biotissue, which cannot be recovered by inherently provided healing capability. This regenerated biotissue has the same form and function as those of original tissue and made with three factors such as a cell, scaffold and a growth factor.

In medical and dental treatments, bone regeneration by using own-bone has been widely used. However, for example, as a medical treatment of periodontal tissue with respect to the periodontosis having a bone deficit in a wide range, a tissue regeneration guide method has been developed. In the tissue regeneration guide method, it is necessary for a cell to keep a preferable interaction with a circumference condition thereof (a cell factor or an extracellular matrix), in order to grow and differentiate in the biotissue in a process during the regeneration of the periodontal tissue and realize the function of the cell. Then, when an initial condition of the regeneration process is suitably set up to thereby actuate self-repairing ability of the tissue according to the regeneration, the deficit part is recovered and repaired to a normal tissue. However, as for supporting tissue (fibrous tissue or a bone) of a tooth destroyed by periodontosis, if waiting the healing without doing anything, another soft tissue such as an epithelium or the like is entered to the necessary supporting tissue before regeneration, and thus there is a problem in which the supporting tissue of the destroyed tooth is not regenerated well. Then, in order to keep a space for regenerating the supporting tissue until regeneration of the necessary supporting tissue, a film-shape material is used to prevent the invasion of the unnecessary tissue, to thereby regenerate the supporting tissue of the tooth (for example, refer to The NIPPON Dental Review "The front line of the regenerative medical treatment on the basis of the biomaterial and the biotissue engineering" written by Yasuhiko TABATA, published by HYORON Publishers Co., Ltd., February 2004, volume 64, No. 2, p. 167-181). As the film-like material used for keeping the space for regenerating the supporting tissue until regeneration of the necessary supporting tissue, a semitransparent film such as an ethylene tetrafluoride resin film, a filter made with polyethylene or the like has been conventionally used. However, since these materials are non-bioabsorbable materials, it is necessary to remove these materials after the operation. Then, in recent years, the medical treatment by the tissue regeneration guide method has been widely used (for example, refer to Japanese Patent No. 2709349, Japanese Patent Application Laid Open No. 2002-085547). This treatment has an advantage that the film can be decomposed and absorbed immediately to vanish after the operation without remaining in the living body as a foreign matter, by using a film comprising a bioabsorbable material made with a bioabsorbable polymer material or a collagen, and thus the operation for removal is not necessary.

However, the tissue according to the regeneration has the low self-repairing ability, and thus the regeneration of the tissue may be hardly done only by preventing the invasion of the unnecessary tissue from the outside. In this case, for example, the following method has been used, that is, the cell, the growth factor or the mixture of those is contained into a polyglycolic acid nonwoven fabric or a porous hydroxyl apatite, and prepared by culturing it during a fixed period, and so obtained product is embedded in an applied part.

For example, a following technique for producing a biotissue filing body is indicated (for example, refer to Japanese Patent Application Laid Open No. 2004-105046). That is, a culture medium is stored in a production device of a biotissue filling body having a filling material layer and a dissolving layer in a container capable of storing, a culture medium. The filling material layer comprises a porous ceramics, collagen, polylactic acid, polyglycolic acid, hyaluronic acid or a material made by mixing those and has biocompatibility and/or bioabsorbability. The dissolving layer comprises a gelatin or the like and covers the upper surface of the filling material layer. When the cell is taken into the culture medium, the cell is precipitated and adhered on the surface of the dissolving layer to be grown along this surface. As time passes, the dissolving layer is dissolved to the culture medium to be disappeared. Thereby, the cell adhered on the dissolving layer adheres on the upper surface of the filling material layer comprising a biotissue filling material, and is grown continuously, where the biotissue filling material is originally existed at a lower part of the dissolving layer. As a result of this, the cell is grown by utilizing the biotissue filling material, to thereby produce the biotissue filling body. However, as for the bioactive ceramics such as calcium phosphate or the like, there is a problem that the cell is hardly grown in a base material. Further, the block-shaped filling material has low shaping property, so that it is difficult to carry out a treatment such as trimming or the like corresponding to the shape of the deficit part.

Further, the following technique for regenerating the tissue is indicated (for example, refer to Japanese Patent Application Laid Open No. 2003-010308). That is, a base material for regenerating cell tissue is formed so as to have various shapes, such as a sheet-shape, film-Shape, fragment-shape, sponge-shape, block-shape, fiber-shape or tube-shape in order to fill it to the deficit part of the tissue. This base material for regenerating cell tissue comprises hyaluronic acid and includes hyaluronic acid gel, which is not substantially modified by the chemical crosslinking agent or the chemical modifying agent, and hardly soluble in a neutral aqueous solution. Thereafter, a cell such as a chondrocyte, a stem cell, a marrow cell, an osteoblast, an ES cell or the like, and a material for guiding cell differentiation if necessary, are contained in the base material. This base material containing the cell and the material is filled to the deficit part in the living body, to thereby regenerate the tissue. At this time, the periosteum may be protected for the purpose of preventing the leakage of the cell, which is grown or migrated, from the deficit part. However, since it requires several weeks for differentiating the stem cell to a bone or a cartilage, the base material is decomposed during culturing of the cell on the base material comprising hyaluronic acid. Thus, there is a problem that the strength of the base material cannot be kept until the cell is transplanted into the deficit part.

Further, for example, the following technique is described for regenerating an alveolar bone (for example, refer to Japanese Patent Application Laid Open No. 2004-024706). That is a material obtained by uniformly mixing granular βtricalcium phosphate and a granular biodegradable material is formed to have a sheet shape, where the biodegradable material is softer than the βtricalcium phosphate. The mixture is heated to near the melting temperature of the biodegradable material to fuse the particles thereby making a porous sheet with remaining spaces between the particles. Thereafter, a sheet (for viable tissue regeneration guide) is prepared by laminating two porous sheets. An antibiotic is impregnated onto one side of the sheet, and a growth factor is impregnated into the other side. When this sheet is arranged by turning the side impregnated with the growth factor to the side of where the alveolar bone should be regenerated, and the side impregnated with the antibiotic to the side of gingiva, the sheet can prevent invasion of another external viable tissue into the space where regeneration of the alveolar bone should be guided. The other external biotissue is, for example, a gingival tissue or the like. Further, when alveolar bone regeneration is guided, the growth factor oozes out into the space and works to promote the growth of the alveolar bone. Then, the antibiotic works against fungi, bacteria or the like in the space where the sheet is provided to guide regeneration. However, the cells just after being removed from a culture dish do not produce sufficient amount of a substrate adhering to the sheet. Thus, there is a problem that the cell is cells are easily removed from the sheet thereby dispersing into a body soon after when it is seeded with the cells and transplanted.

In addition to this, a bone regenerating sheet is also indicated (for example, refer to Japanese Patent Application Laid Open No. 2003-275294). The bone regenerating sheet is made by laminating a cultured cell sheet and a biodegradable sheet, where the cultured cell sheet is made by culturing a mesenchymal stem cell into a sheet shape, and the biodegradable sheet is made of biodegradable substances shaped into a sheet. This sheet is transplanted to the deficit part, blocks the invasion of the tissue cell around the defect part to the deficit part, and promoting an osteogenic action. Thereby, the bone regenerating sheet can increase the repairing speed of the bone defect part. The bone regenerating sheet is made by sticking the cultured cell sheet to the biodegradable sheet using, for example, a fibrin paste or the like. The cultured cell sheet is made by the steps of cultured the mesenchymal stem cell on a culture dish, lowering the temperature of the culture dish to the predetermined temperature being lower than the culture temperature, and exfoliating it from the culture dish. The biodegradable sheet comprises, for example, the collagen or the like. However, the mesenchymal stem cell has multiple differentiation potency and, for example, according to an animal experiment, the property of differentiation to a bone, a cartilage, a fat, a blood vessel, a cardiac muscle or the like is proved. Thus, when the mesenchymal stem cell is transplanted to the defect part as it is, the cell may not be differentiated to the objective tissue.

In addition to the mesenchymal stem cell, another technique for regenerating cartilage is indicated (for example, refer to Japanese Patent Application Laid Open No. 10 (1998)-234844). In this technique, the chondrocyte is seeded in a material comprising the biodegradable polymer formed to have the sponge shape, grown, and embedded in the living body, to thereby regenerate the cartilage tissue. However, when the chondrocyte is used for regeneration of the cartilage tissue, the cartilage of a patient is taken out, cultured and grown at first, but it is hard to grow the chondrocyte in a culture system. Further, the regeneration efficiency of the cartilage tissue of the deficit part is low, and thus the burden given to a patient is large.

SUMMARY OF THE INVENTION

The primary objective of the present invention is to provide the sheet for guiding regeneration of mesenchymal tissue and the production method thereof. This sheet can be easily formed to have an objective shape, keep strength capable of keeping a space for regenerating supporting tissue until the tissue is regenerated, has a property to be decomposed and absorbed after the desired period having passed, and efficiently guide regeneration of mesenchymal tissue.

The earnest work was carried out in order to solve the above-mentioned problems and, as a result of this, the followings were found out to complete the present invention. That is, a mesenchymal cell taken from biotissue is seeded on a surface of the porous sheet containing a culture medium comprising a bioabsorbable polymer material. The mesenchymal cell such as a mesenchymal stem cell, a periodontal ligament cell or the like is cultured on the sheet surface and differentiated to a mesenchymal precursor cell being suitable for guiding regeneration of a deficit part. Then, the cell is firmly adhered to the sheet surface by an extracellular matrix secreted in the differentiation process. When the sheet is embedded into the deficit part, it can be embedded in the state where the cell can easily guide regeneration of tissue of the deficit part without exfoliating from the sheet and dispersing inside a body. Therefore, a sheet for guiding regeneration of mesenchymal tissue can be produced, where the sheet has the ability for efficiently guiding the tissue regeneration.

That is, the present invention relates to a sheet for guiding regeneration of mesenchymal tissue, wherein a mesenchymal precursor cell and an extracellular matrix are adhered on a surface of a porous sheet comprising a bioabsorbable polymer material and containing a culture medium, the mesenchymal precursor cell is differentiated from a mesenchymal cell taken from biotissue, and the extracellular matrix is secreted in the process in which the mesenchymal cell is differentiated to the mesenchymal precursor cell. Further, the present invention relates to the production method of the sheet for guiding regeneration of mesenchymal tissue, the method comprising the steps of containing the culture medium in the surface of the porous sheet made by freezing the bioabsorbable polymer material dissolved with an organic solvent and drying it, seeding the mesenchymal cell grown after taking from biotissue, and differentiating the mesenchymal cell to the mesenchymal precursor cell.

Further, in the present invention, as for the bioabsorbable polymer material, it is preferable to select at least one kind from following polymers, that is, polyglycolic acid, polylactic acid, a copolymer of lactic acid and glycolic acid, poly-ε-caprolactone, a copolymer of lactic acid and ε-caprolactone, polyamino acid, polyortho ester, polymalic acid and a copolymer of those. As the mesenchymal cell taken from biotissue, the mesenchymal stem cell or the periodontal ligament cell is suitable. Further, as the mesenchymal precursor cell, an osteoblast, a chondrocyte, a lipoblast or a myoblast is suitable.

As for the sheet for guiding regeneration of mesenchymal tissue produced by using the method of the present invention, the following effects can be obtained. That is, since the mesenchymal cell taken from biotissue is seeded on the surface of the porous sheet comprising the bioabsorbable polymer material and containing the culture medium, and differentiated to the mesenchymal precursor cell, which is suitable for guiding the regeneration of the deficit part, on the sheet surface, thus, the cell is firmly adhered to the sheet surface by the extracellular matrix secreted in the differentiation process, the cell is not exfoliated from the sheet and not dispersed inside the living body when the sheet is embedded into the deficit part, and the sheet can be embedded in the state where the cell can easily guide regeneration of tissue of the deficit part. Therefore, the sheet for guiding regeneration of mesenchymal tissue, which has ability for efficiently guiding the tissue regeneration, can be produced. Further, since having the sheet shape, the sheet can be easily formed to have the objective shape, and the strength capable of securing the space for regenerating supporting tissue can be kept until regenerating the tissue. Further, since the sheet is the bioabsorbable sheet, it is decomposed and absorbed in the living body after elapse of the desired period, so that, it is not necessary to carry out the removing operation.

When the sheet for guiding regeneration of mesenchymal tissue according to the present invention is used, for example, the regeneration of the mesenchymal tissue, such as a cranium, a jawbone, a long tubular bone such as a thighbone or the like, an iliac bone, a backbone or the like, is guided.

Further, as for the production method of the sheet for guiding regeneration of mesenchymal tissue according to the present invention, since the sheet for guiding regeneration of mesenchymal tissue is made by simple steps of containing a culture medium in the surface of a porous sheet produced by freezing and drying a bioabsorbable polymer material dissolved with an organic solvent, seeding a mesenchymal cell grown after taking from biotissue, and differentiating the mesenchymal cell to a mesenchymal precursor cell, thus, the sheet can be easily produced with a low cost.

DETAILED DESCRIPTION OF PREFERRED EMBODIMENT

The mesenchymal cell used in the present invention can regenerate mesenchymal tissue such as a bone, cartilage, fat or muscle cell or the like. The mesenchymal cell can have the ability of promoting the regeneration of these tissues. For example, the mesenchymal stem cell, the periodontal ligament cell or the like can be used. As a method for taking the cell, a conventional method used in a medical field can be used without special limitation. For example, sources for cells include bone marrow from pelvic bone (an iliac bone), long bone from arms and legs (a thighbone, a tibia), periosteum, an alveolar bone or the like, a periosteum of a palate, a periodontal ligament (a periodontal membrane) or the like. In these sources, the bone marrow of the iliac bone, the breastbone, the alveolar bone or the like, the periodontal membrane of the palate, the alveolar bone or the like are preferable, as it is possible to carry out an easy operation with a minimum exfoliation and incision of the skin and muscle when taking the cell.

The sheet for guiding regeneration of mesenchymal tissue made by the present invention can be applied in the following medical cases. In a dental area, for example, it can be applied for the regeneration of mesenchymal tissue lost by periodontosis, a cleft palate, and bone filling to a jawbone and a jawbank. In a surgical area, it can be applied for bone filling for a broken bone and an iliac bone deficit or the like by a surgical operation. Further, it can be applied for myocardial infarction. In a brain surgical area, it can be applied for bone filling for a cranium deficit or the like by a surgical treatment. In an orthopedics area, it can be applied for bone filling for an iliac bone deficit or the like by an orthopedics operation, and applied for filling for a backbone and an intervertebral disc. Further, it can be applied for filling for a knee cartilage deficit and an osteoarthritis by a dyskinesia or the like. In a dermatology area, it can be applied for regeneration in case of an intractable dermal disease such as decubitus ulcer or the like, and an external injury by a burn or the like. In a plastic surgical area, it can be applied for the deficit of a bone, a cartilage and a muscle by a plastic surgical operation. For example, it can be applied for regeneration of a maxillofacial or finger deficit by a traffic accident. Further, it can be applied for forming a chest and regenerating a breast. It can be applied for filling and forming with respect to deficits of bone, cartilage, fat and muscle in a cosmetic and aesthetic appreciation surgery.

The taken mesenchymal cell is cultured to be remarkably amplified during 1 to 2 weeks in a culture dish for culturing tissue. As a culture medium, suitable culture mediums can be used, but it is preferable to use DMEM (Dulbeco's Modified Eagle Medium) culture medium for culturing a cell, which contains self serum, fetal bovine serum (FBS), for example. At this time, when a specific growth factor (for example, bFGF) is worked, the mesenchymal cell is increased while keeping the high multiple differentiation potency, to thereby promote the regeneration of the mesenchymal tissue, so that remarkable regenerating ability can be obtained.

Then, the mesenchymal cell, which is cultured to be remarkably amplified while keeping the multi differentiation potency under existence of the specific growth factor, is exfoliated from the culture dish through a trypsin treatment and seeded on the surface of a porous sheet comprising a bioabsorbable polymer material and containing a culture medium. As the bioabsorbable polymer material constituting the porous sheet, at least one kind selected from following polymers can be used, that is, polyglycolic acid, polylactic acid, a copolymer of lactic acid and glycolic acid, poly-ε-caprolactone, a copolymer of lactic acid and ε-caprolactone, polyamino acid, polyortho ester, polymalic acid and a copolymer of those. The porous sheet is produced by steps of freezing the bioabsorbable polymer material dissolved with an organic solvent, such as dioxane, chloroform, dichloromethane, carbon tetrachloride, acetone or tetrahydrofuran, and drying it. As such the porous sheet, a film or sheet-shaped one having a porous and uniform structure can be suitably used. For example, a material only comprising the copolymer of lactic acid and ε-caprolactone or the copolymer of lactic acid and glycolic acid, as indicated in Japanese Patent No. 2709349, is used as the biodegradable and absorbable polymer material. This copolymer has a weight average molecular amount of 50,000 to 500,000, a composition mol ratio of 95:5 to 5:95 mol %, a kinematic viscoelasticity ratio of $5 \times 10^7$ to $5 \times 10^9$ dyne/cm$^2$, elongation percentage being within the range of 100 to 2,000% and a thickness of 10 to 500 μm. Further, the culture medium capable of culturing the mesenchymal cell is contained in the surface of the porous sheet. As a method for containing the culture medium in the surface of the porous sheet, a method of dipping the porous sheet in the culture medium for overnight is preferable.

Then, the mesenchymal cell is differentiated to the objective mesenchymal precursor cell being suitable for the deficit tissue, after seeding it in the surface of the porous sheet comprising the bioabsorbable polymer material and containing the culture medium. For example, when the deficit part is in the bone, the cell may be differentiated to the osteoblast by culturing it for 3 to 4 weeks by using a culture medium indicated in Science 284, 143-147, 1999. Then, the seeded mesenchymal cell secretes the extracellular matrix peculiar to the osteoblast as it differentiates to the osteoblast, and the special characters, such as high alkaline phosphatase activity, deposited calcium concentration, and stainability by an alizarin red indicating the mineralization appear for example. Further, osteocalcine mRNA peculiar to the osteoblast appears.

Where the mesenchymal cell differentiates to a mesenchymal precursor cell on the surface of the porous sheet, the differentiated mesenchymal cell produces the extracellular matrix suitable for increasing the adherence of the cell to the matrix so that it is firmly adhered to the surface of the porous sheet. Further, when the porous sheet is embedded into the deficit part of the body for regeneration, the cell does not release from the porous sheet into the living body. Thus, the sheet can be embedded such that the cell can easily guide the regeneration of the tissue.

Example

Hereinafter, the present invention is explained with examples, but the present invention is not limited to these examples.
Preparation of the Mesenchymal Stem Cell
Mesenchymal Stem Cell A (a Mesenchymal Stem Cell Taken from Human Iliac Bone Marrow)

A cell taken from the human iliac bone marrow was suspended with a 10% FBS and DMED culture medium, and $1\times10^5$ nucleated cells were seeded in a cell culture dish having the diameter of 10 cm, to thereby culture the cells under existence of 5% carbon dioxide gas at 37° C. By exchanging the culture medium on the third day, a non-adherent cell (a hematopoietic cell) was removed. After that, the culture medium was exchanged every three days. A basic fibroblast growth factor (bFGF) was added to the culture medium at a ratio of 3 ng/ml on and after the fifth day. As a result of this, the cells were increased to be approximate-confluent around the 10th day. The cell culture dish was incubated for 5 minutes with 0.05% trypsin and 0.2 mMEDTA to thereby isolate the cells. The number of the cells was measured by a Coulter counter (Z1 single, made by Coulter Corporation), and these cells were seeded in the 10% FBS and DMEM culture medium in the cell culture dish with the density of 5000 cells/cm². The culture dish has the diameter of 10 cm. A third passage cell obtained from an approximate-confluent second subculture medium made by repeating this operation was named as the mesenchymal stem cell A.
Mesenchymal Stem Cell B (a Mesenchymal Stem Cell Taken from a Marrow of the Thighbone and the Shinbone of a Rat)

The muscle and the ligament were removed from the thighbone and the shinbone of a rat for four-week age, and the both ends of the thighbone and the shone bone were cut. The inside of the bone was washed with the 10% FBS and DMEM culture medium, and the marrow is loosened by fully suspended in the washing liquid. Then, it was centrifuged for 5 minutes with 300 G to isolate the cells, to thereby obtain nucleated cells. The $3.75\times10^7$ nucleated cells obtained from the marrow were seeded in the DMEM culture medium in a 75 cm² culture flask as same as the above DMEM culture medium, to thereby culture the cells under existence of 5% carbon dioxide gas at 37° C. By exchanging the culture medium on the third day, the non-adherent cell (the hematopoietic cell) was removed. After that, the culture medium was exchanged every three days. The bFGF was added to the culture medium at the ratio of 3 ng/ml on and after the fifth day. As a result of this, the cells were increased to be approximate-confluent around the 10th day. The culture flask was incubated for 5 minutes with 0.05% trypsin and 0.2 mMEDTA to thereby isolate the cells. The number of the cells was measured by the Coulter counter (Z1 single, made by Coulter Corporation), and these cells were seeded in the 10% FBS and DMEM culture medium in the 75 cm² culture flask with the density of 5000 cells/cm². The third passage cell obtained from the approximate-confluent second subculture medium made by repeating this operation was named as the mesenchymal stem cell B.
Mesenchymal Stem Cell C (the Periodontal Ligament Cell Taken from a Extracted Human Tooth)

A healthy tooth, which was conveniently extracted by the reason of an orthodontic treatment, was disinfected for three seconds with a 70% ethanol solution, and ⅓ of the crown side and ⅓ of the root tip side of the periodontal ligament were removed by using a scalpel. Then, it was dipped in the DMEM containing 2.0 mg/ml collagenase and 2.5 mg/ml trypsin, to thereby work it by shaking for 30 minutes at 37° C. After that, the cell was washed by centrifuging (150 G×5 min), and the obtained cell component was suspended with the 10% FBS and DMEM culture medium. Then, $1\times10^6$ nucleated cells were seeded to a culture dish having the diameter of 10 cm, to thereby culture the cells under existence of 5% carbon dioxide gas at 37° C. By exchanging the culture medium on the third day, the non-adherent cell (the hematopoietic cell) was removed. After that, the culture medium was exchanged every three days. The basic fibroblast growth factor (bFGF) was added to the culture medium at the ratio of 3 ng/ml on and after the fifth day. As a result of this, the cells were increased to be approximate-confluent around the tenth day. The culture dish was incubated for 5 minutes with 0.05% trypsin and 0.2 mMEDTA to isolate the cells. The number of the cells was measured by the Coulter counter (Z1 single, made by Coulter Corporation), and these cells were seeded in the 10% FBS and DMEM culture medium in the culture dish having the diameter of 10 cm with the density of 5000 cells/cm². The third passage cell obtained from the approximate-confluent second subculture medium made by repeating this operation was named as the mesenchymal stem cell C.
<Preparation of the Porous Sheet>
Porous Sheet X (Polymer Material: Copolymer of Lactic Acid and Glycolic Acid)

A porous sheet having the film thickness of 250 μm was obtained by the steps of taking the copolymer of lactic acid and glycolic acid (lactic acid:glycolic acid=75:25, the weight average molecular amount was about $2\times10^5$) into dioxane to be 10% concentration, stirring it to dissolve by a stirrer, taking the solution into a glass mold to be frozen by a freezer at the condition of −30° C., drying it for 48 hours under a reduced atmosphere by a vacuum dryer to remove the dioxane, and taking out it from the mold to be pressed. Then, the porous sheet X containing the culture medium was produced by γ-sterilizing the obtained porous sheet, and dipping it overnight in the 10% FBS and DMEM culture medium.
Porous Sheet Y (Polymer Material: Polylactic Acid)

A porous sheet having the film thickness of 250 μm was obtained by the steps of taking the polylactic acid (the weight average molecular amount was about $2\times10^5$) into dichloromethane to be 6% concentration, stirring it to dissolve by the stirrer, taking it into a glass mold to be frozen by the freezer at the condition of −30° C., drying it for 48 hours under the reduced atmosphere by the vacuum dryer to remove the dichloromethane, and taking out it from the mold to be pressed. Then, the porous sheet Y containing the culture medium was produced by γ-sterilizing the obtained porous sheet, and dipping it overnight in the 10% FBS and DMEM culture medium.

Porous Sheet Z (Polymer Material: Copolymer of Lactic Acid and ε-Caprolactone)

A porous sheet having the film thickness of 250 μm was obtained by the steps of taking the copolymer of lactic acid and ε-caprolactone (lactic acid: ε-caprolactone=75:25, the weight average molecular amount was about $2\times10^5$) into dioxane to be 6% concentration, stirring it to dissolve by the stirrer, taking it into a glass mold to be frozen by the freezer at the condition of −30° C., drying it for 48 hours under the reduced atmosphere by the vacuum dryer to remove the dioxane, and taking out it from the mold to be pressed. Then, the porous sheet Z containing the culture medium was produced by γ-sterilizing the obtained porous sheet, and dipping it overnight in the 10% FBS and DMEM culture medium.

Example 1

A sheet for guiding regeneration of bone tissue was made by the steps of seeding the mesenchymal stem cell A to the porous sheet X with a density of about 20,000 cells/cm², and culturing it for 4 weeks, while exchanging the culture medium every three days, under existence of 5% carbon dioxide gas at 37° C., where the cell A was suspended in the culture medium for osteogenic differentiation (αMEM, L-glutamine 2 mM, 10% FBS, $10^{-7}$M dexamethasone, 50 μg/ml ascorbic acid 2 phosphoric acid, 10 mM β glycerophosphoric acid). The sheet for guiding regeneration of bone adhered with the osteoblast and the extracellular matrix was thus made, where the osteoblast was the mesenchymal precursor cell.

Example 2

A sheet for guiding regeneration of bone was made by the steps of seeding the mesenchymal stem cell B to the porous sheet Z with the density of about 20,000 cells/cm², and culturing it for 3 weeks, while exchanging the culture medium every three days, under existence of 5% carbon dioxide gas at 37° C., where the cell B was suspended in the culture medium for osteogenic differentiation (αMEM, L-glutamine 2 mM, 10% FBS, $10^{-7}$M dexamethasone, 50 μg/ml ascorbic acid 2 phosphoric acid, 10 mM β glycerophosphoric acid). The sheet for guiding regeneration of bone adhered with osteoblast and the extracellular matrix was thus made, where the osteoblast was the mesenchymal precursor cell.

Example 3

A sheet for guiding regeneration of bone was made by the steps of seeding the mesenchymal stem cell A to the porous sheet X with the density of about 20,000 cells/cm², and culturing it for 4 weeks, while exchanging the culture medium every three days, under existence of 5% carbon dioxide gas at 37° C., where the cell A was suspended in the culture medium for chondrogenic differentiation (αMEM, L-glutamine 2 mM, glucose 4.5 mg/ml, $10^{-7}$M dexamethasone, 50 μg/ml ascorbic acid 2 phosphoric acid, 10 ng/ml TGF-β, 6.25 μg/ml insulin, 6.25 μg/ml transferrin, 6.25 ng/ml selenic acid, 5.33 μg/ml linolenic acid, 1.25 mg/ml bovine serum albumin). The sheet for guiding regeneration of cartilage adhered with the chondrocyte and the extracellular matrix was thus made, where the chondrocyte was the mesenchymal precursor cell.

Example 4

A sheet for guiding regeneration of adipose was made by the steps of seeding the mesenchymal stem cell A to the porous sheet X with the density of about 20,000 cells/cm², culturing it for 2 days under existence of 5% carbon dioxide gas at 37° C., exchanging thereafter the culture medium to a culture medium for keeping differentiation of fat (DMEM, Hi glucose, 10% FBS, 10 g/ml insulin), and culturing it for 20 days while exchanging the culture medium for guiding the differentiation of fat every two days and the culture medium for keeping differentiation of fat every three days respectively, where the cell A was suspended in the culture liquid for guiding differentiation of fat (DMEM, Hi glucose, 10% FBS, 10 μg/ml insulin, 0.2 mM indomethacin, $10^{-6}$M dexamethasone, 0.5 mM3-isobutyl-1-methylxanthine). The sheet for guiding regeneration of fat tissue adhered with the bone blast cell and the extracellular substrate was thus made, where the bone blast cell was the mesenchymal tissue precursor cell.

Example 5

A sheet for guiding regeneration of bone was made by the steps of seeding the mesenchymal stem cell C to the porous sheet X with the density of about 20,000 cells/cm², and culturing it for 3 weeks, while exchanging the culture medium every three days, under existence of 5% carbon dioxide gas at 37° C., where the cell C was suspended in the culture medium for osteogenic differentiation (DMEM, L-glutamine 2 mM0, 10% FBS, $10^{-7}$M dexamethasone, 50 μg/ml ascorbic acid 2 phosphoric acid, 10 mM glycerophosphoric acid). The sheet for guiding regeneration of bone adhered with the osteoblast and the extracellular matrix was thus made, where the osteoblast was the mesenchymal precursor cell.

As for the sheets for guiding regeneration of tissue indicated in the above examples, the followings were found out. That is, the mesenchymal precursor cell differentiated from the mesenchymal cell was firmly adhered to the surface of the porous sheet by the extracellular matrix, which was secreted in the process of the mesenchymal cell being differentiated to the mesenchymal precursor cell. The sheet is flexible and can easily guide regeneration of tissue of the deficit part. Therefore, the sheet has extremely high value for contributing to the medical treatment.

What is claimed is:

1. A method to regenerate mesenchymal tissue, the method comprising:
    freezing a bioabsorbable polymer material in a solvent and then drying the bioabsorbable polymer material to form a porous sheet,
    adhering mesenchymal cells to the porous sheet in a culture medium, and
    culturing the porous sheet comprising the mesenchymal cells in the culture medium under conditions that generate an extracellular matrix and differentiate the mesenchymal cells into the mesenchymal tissue;
    wherein the bioabsorbable polymer material is at least one material selected from the group consisting of polyglycolic acid, polylactic acid, poly-ε-caprolactone, polyamino acid, polymalic acid, and copolymers thereof.

2. The method as claimed in claim 1, wherein the mesenchymal cells are mesenchymal stem cells or periodontal ligament cells.

3. The method as claimed in claim 2, wherein the culture medium is Dulbeco's Modified Eagle Medium (DMEM) containing serum.

4. The method as claimed in claim 1, wherein the mesenchymal cells are bone blast cells, cartilage blast cells, fat blast cells, or myoblast cells.

5. The method as claimed in claim 1, wherein the bioabsorbable polymer material is at least a copolymer of lactic acid and glycolic acid, and the mesenchymal cells are mesenchymal stem cells.

6. The method as claimed in claim 1, wherein the culture medium is Dulbeco's Modified Eagle Medium (DMEM) containing serum.

7. The method as claimed in claim 1, wherein the culture medium further comprises basic fibroblast growth factor (bFGF).

* * * * *